United States Patent [19]

Kligman

[11] Patent Number: 5,026,691
[45] Date of Patent: Jun. 25, 1991

[54] COMBINATION OF MINOXIDIL AND AN ANTIINFLAMMATORY AGENT FOR TREATING PATTERNED ALOPECIA

[75] Inventor: Albert M. Kligman, Philadelphia, Pa.

[73] Assignee: The Upjohn Company, Kalamazoo, Mich.

[21] Appl. No.: 415,077

[22] Filed: Sep. 29, 1989

Related U.S. Application Data

[63] Continuation-in-part of Ser. No. 55,674, May 29, 1987, abandoned, which is a continuation-in-part of Ser. No. 32,362, Mar. 30, 1987, abandoned.

[51] Int. Cl.$^5$ ..................... A01N 45/00; A01N 43/54; A01N 37/10
[52] U.S. Cl. .................................. 514/171; 514/275; 514/570; 514/880
[58] Field of Search ........................ 514/171, 275, 880

[56] References Cited

U.S. PATENT DOCUMENTS 4,139,619  2/1979  Chidsey, III ........................ 424/45
4,596,812  6/1986  Chidsey, III et al. ............... 514/256

FOREIGN PATENT DOCUMENTS 0129197  12/1984  European Pat. Off. ............ 514/880
0220118   4/1987  France .
US82/02833  3/1981  PCT Int'l Appl. .
US83/02558 11/1982  PCT Int'l Appl. .
US85/04577  4/1985  PCT Int'l Appl. .
US86/00073  7/1986  PCT Int'l Appl. .

OTHER PUBLICATIONS

The Merck Index, Tenth Edition (1983), p. 693.

*Primary Examiner*—Stanley J. Friedman
*Assistant Examiner*—Theodore J. Criares
*Attorney, Agent, or Firm*—Lawrence T. Welch

[57] ABSTRACT

This invention relates to the method for treating human baldness, including the form of alopecia commonly known as "male pattern baldness", which comprises regular topical application to the affected areas of the human scalp of minoxidil and an anti-inflammatory agent.

9 Claims, No Drawings

COMBINATION OF MINOXIDIL AND AN ANTIINFLAMMATORY AGENT FOR TREATING PATTERNED ALOPECIA

CROSS REFERENCE TO RELATED APPLICATIONS

This application is a continuation of PCT Application PCT/US88/00870, filed Mar. 23, 1988, now abandoned; which was a continuation-in-part of U.S. Ser. No. 07/055,674, filed May 29, 1987, now abandoned; which was a continuation-in-part of U.S. Ser. No. 07/032,362, filed Mar. 30, 1987, now abandoned.

BACKGROUND

The present invention relates to methods, and compositions for treating human patterned alopecia, also called androgenic alopecia involving the use of minoxidil (or related compounds) and antiinflammatory agents.

Dermatologists recognize many different types of hair loss, the most common by far being "androgenic alopecia" wherein human males begin losing scalp hair at the temples and on the crown of the head in early adult life. This type of hair loss is more common and more severe in males, hence its common name "male pattern baldness". However, similar patterned baldness occurs in women, though it progresses more slowly and does not reach the end stage of complete denudation. An effective treatment for these and related conditions has long been sought.

There are two types of hair follicles which produce either "terminal hairs" or "vellus hairs". Terminal hairs are coarse, pigmented, long hairs in which the bulb of the follicle is situated deep in the skin, usually in the subcutaneous tissue. Vellus hairs, on the other hand, are fine, thin, non-pigmented short hairs whose bulbs are located superficially in the upper dermis. In patterned alopecia, follicles which produce terminal hairs are gradually converted to vellus ones through a miniaturization process.

Along with this progressive involution there inevitably occurs changes in the proportion of hairs in the various phases of the hair cycle. All follicles pass through a life cycle that includes three phases, namely, (1) anagen (2) catagen and (3) telogen. The anagen phase is the period of active hair growth and, on the scalp generally lasts from 3-6 years. Catagen is a short transitional phase when the follicle contracts in preparation for a resting period. It lasts a couple of weeks. In telogen, the follicle is in a resting phase where all growth ceases and the hair becomes short "club" hairs. When a new cycle begins, the club hair is shed. Telogen scalp hairs are relatively short-lived, about three to four months.

Normally, approximately 90% of scalp hairs are in the anagen phase, less than 1% in catagen and the remainder in telogen. With the onset of patterned baldness, a successively greater proportion of hairs are in the telogen phase, with correspondingly fewer in the active growth anagen phase.

Additionally, there may be some actual loss of hair follicles but this is limited to the last final phase. For the most part, the visible diminution in the bulk of hair is due to the miniaturization of the follicles. In completely bald areas, all the follicles are in the vellus phase producing ugly fine, short, non-pigmented hairs which are cosmetically useless. It may take 20 to 30 years for the distinctly anagen follicles on the crown to become transformed into a uniform population of vellus follicles.

Patterned baldness is sometimes called androgenic alopecia because male hormones are necessary for its development. It does not occur before adolescence, nor in castrates. Attempts to prevent alopecia by hormonal treatments by using anti-androgens or female hormones have failed. A hereditary component is also recognized since patterned alopecia runs in families. Despite intensive investigation, the mechanism whereby terminal follicles convert to vellus ones is unknown.

At the present time, one effective treatment for patterned alopecia is hair transplantation. Plugs of hair-bearing skin from the back of the scalp are transplanted into the bald areas. The procedure is costly and painful. Hundreds of plugs must be transplanted to create an appearance of hairiness. It is impossible to obtain anything near the original density of terminal hair.

Many other approaches for creating or reversing patterned alopecia have been tried including ultra-violet radiation, massage, chemical irritation and innumerable natural products and herbs. None of these has been generally accepted as effective.

Drugs offer a more rational approach—though for the most part have been designed to interfere with drug metabolism. The results have been poor to date. In Europe, a schedule of estrogens and antiandrogens have been administered orally to balding females with inconsistent results and with obvious limitations.

The androgenic hormone testosterone has been shown to stimulate hair growth when injected into the beard and pubic regions of adult females. Also, topical application to the armpit causes increased hair growth in aged persons. Nonetheless, topical application of testosterone has not been able to grow hair in balding individuals. Indeed, high doses of oral testosterone can induce patterned alopecia.

The topical application of minoxidil is currently the most effective therapy for patterned alopecia. Minoxidil is a well-known pharmaceutical agent marketed by The Upjohn Company in the form of LONITEN ® Tablets for the treatment of hypertension. Numerous investigators have demonstrated that it can stimulate visible hair growth in a majority of balding subjects. The structure and use of this compound is described in U.S. Pat. Nos. 4,139,619 and 4,596,812. This compound has varying degrees of efficacy for moderating androgenic alopecia, depending on the degree of baldness, its duration, the age of the patient and, of course, on the concentration of the drug in an appropriate vehicle.

The present invention provides a novel, non-obvious and effective treatment for patterned male and female alopecia.

INFORMATION DISCLOSURE

U.S. Pat. No. 4,596,812 discloses the use of minoxidil. 6-amino-1,2-dihydro-1-hydroxy-2-imino-4-piperidinopyrimidine, as a therapeutic agent to treat alopecia and arrest and reverse male pattern alopecia. U.S. Pat. No. 4,139,619 discloses the use of minoxidil and related 6-amino-4-(substituted amino)-1,2-dihydro-1-hydroxy-2-imino-pyrimidines as a means for (a) increasing the rate of growth of terminal hair, and (b) converting vellus hair to growth as terminal hair.

The use of retinoids alone or in combination with minoxidil and related substituted pyrimidines to increase hair growth is disclosed in PCT publication numbers US85/04577, PCT US83/02558 and PCT US82/02833.

The use of minoxidil sulfate (2,6,-diamino-4-(1-piperidinyl)-1-(sulfooxy)-pyrimidinium hydroxide, inner salt) as a therapeutic agent to stimulate hair growth is disclosed in PCT Application US86/00073 published July 31, 1986.

Topical antiinflammatory agents, such as hydrocortisone, are known, see, e.g., The Merck Index, Tenth Edition, 4689 (1983).

Japanese patent Kokai 61-260010 states that topical minoxidil formulations containing. e.g., amino acids, bactericides, antiinflammatory agents, adrenal hormones, antihistaminics, vitamin E derivatives, estrogens, and capillary vessel dilators may be prepared. No formulation containing minoxidil and the antiinflammatory agents described herein is disclosed or suggested.

SUMMARY OF THE INVENTION

The present invention particularly provides:

(1) a method of treating humans for patterned alopecia which comprises the concomitant administration to a human susceptible to said alopecia:

(a) an effective amount of minoxidil, administered topically to the scalp; and (b) an anti-inflammatory compound, administered topically or orally;

(2) a topical pharmaceutical composition for the treatment of alopecia consisting of an amount effective to treat alopecia of minoxidil and an anti-inflammatory compound in a vehicle suitable for topical application; and (3) the method in (1) wherein the anti-inflammatory agent is topically applied to the scalp.

By "concomitant administration" or "combination" is meant simultaneous or sequential administration of the two agents. These can be administered in any order, or can be administered together in one topical composition.

By minoxidil is meant the 2,4-pyrimidinediamine, 6-(1-piperdinyl)-3-oxide, and analogs and salts thereof, as described in U S. Pat. Nos. 4,139,619 and 4,596,812, which patents are incorporated by reference herein.

The use of topical minoxidil compositions in the treatment and prevention of baldness is well known to an ordinarily skilled physician or dermatologist. In addition, this use is set forth in U.S. Pat. Nos. 4,139,619 and 4,596,812, expressly incorporated by reference herein. Similar methods can be used for the instant invention.

By anti-inflammatory agent is meant any agent known to reduce inflammation by oral or topical administration and includes both steroidal (e.g. corticosteroids) and non-steroidal (e.g. ibuprofen and its derivatives) compounds. Steroidal compounds are used in a concentration of 0.5 to 2.5% and non-steroidals are used in a range of 1 to 5%. Such anti-inflammatory agents are well known to a physician of ordinary skill. See. e.g., Medical Pharmacology, pp. 331–343 9th Edition (1978). These agents may be orally or topically administered. For ease of administration, simultaneous topical application of minoxidil and the anti-inflammatory agent (undertaken in a combined composition), may be preferred. However, in cases of severe inflammation, oral administration of the anti-inflammatory agent concomitant with topically administered minoxidil may be preferred.

Surprisingly, the present inventor has discovered that there is a chronic inflammatory process, subtending to the hair bulbs, in patterned alopecia, leading to eventual scarring of the lower follicle, making regrowth impossible. The present invention solves this problem by suppressing sub-bulbar inflammation, thus allowing for regrowth.

Thus, this invention relates to the method for treating androgenic alopecia, both male and female, using a topical application of a pharmaceutical composition containing minoxidil and an antiinflammatory compound. An ordinary skilled physician or dermatologist can readily identify those humans susceptible to patterned alopecia who are in need of such treatment.

The percentage by weight of the compound of the minoxidil herein utilized typically ranges from about 0.1% to about 10.0% of the preparation, preferably from about 1% to about 5% and in these preparations the carrier or vehicle constitutes a major amount of the preparation.

The compositions encompassed by this invention include formulations adapted for topical application to the human scalp. Conventional pharmaceutical preparations for this purpose include ointments, lotions, pastes, jellies, gels, mousses, sprays, foams, aerosols, and the like. The term "ointment" embraces formulations which include creams which are either oil-in-water or water-in-oil emulsions. The compounds may also be formulated into liposomal preparations or lipid emulsions or dissolved in conventional solvents such as alcohol, propanol, and the like.

The pharmaceutical preparations of the subject invention are applied on a regular basis, with or without occlusion, for a period of time sufficient to effect hair growth. Occlusion of the preparation may be obtained by any conventional means such as bandages, plastic coverings, shower caps swimming caps, etc. The percentage of active ingredients as well as frequency of application may be varied as necessary or desirable to achieve the desired results.

DESCRIPTION OF THE PREFERRED EMBODIMENT

The present invention is seen more by fully the examples given below.

EXAMPLE 1

Fifteen males with early alopecia were treated with a combination of 2% minoxidil and 1% hydrocortisone in a hydroalcoholic vehicle. The subjects were shampooed weekly and hairs were counted after filtration. Fewer hairs were observed to be shed as treatment progressed. Hair regrowth has been substantially better than with minoxidil alone in comparable cases. The longest period of treatment is 6 months. Hair loss has virtually stopped in all subjects.

EXAMPLE 2

Twenty-six young-adult, balding white males were treated for at least five months with a hydroalcoholic solution containing: (1) 3% minoxidil; and (2) 2.5% hydrocortisone. These subjects were in an early stage of baldness, not exceeding 2 inches in diameter over the vertex.

The combination formulation stimulated hair growth in these subjects within three months. Most of the subjects volunteered comments of surprise that enhancement could be seen as early as two months. These results were compared with the results of a study at the same clinic of 50 patients using 3% minoxidil alone. In the opinion of the investigator, hair growth was seen sooner and on a greater proportion of patients in the group treated with the combination of minoxidil and an antiinflammatory agent.

I claim:

1. A method of treating humans for patterned alopecia which comprises the concomitant administration to a human susceptible to said alopecia of an effective amount of:
   (a) minoxidil, administered topically; and
   (b) an anti-inflammatory compound, selected from the group consisting of steroidal and non-steroidal anti-inflammatory agents, administered topically or orally.

2. A topical pharmaceutical composition for the treatment of alopecia consisting of an amount effective to treat alopecia of minoxidil and an anti-inflammatory compound, selected from the group consisting of steroidal and non-steroidal anti-inflammatory agents, in a vehicle adapted for topical application.

3. A method of claim 1, wherein the anti-inflammatory agent is topically applied to the scalp.

4. A method of claim 3, wherein minoxidil is applied at a concentration of 2% and hydrocortisone is applied topically at a concentration of 1%.

5. A composition of claim 1, containing 2% minoxidil and 1% hydrocortisone.

6. A method of claim 3, wherein minoxidil is applied topically at a concentration of 3% and hydrocortisone is topically applied at a concentration of 2.5%.

7. A composition of claim 1, containing 3% minoxidil and 2.5% hydrocortisone.

8. A method of claim 1, wherein the steroidal anti-inflammatory agent is a corticosteroid and the non-steroidal anti-inflammatory agent is ibuprofen or a derivative.

9. A composition of claim 2, wherein the steroidal anti-inflammatory agent is a corticosteroid and the non-steroidal anti-inflammatory is ibuprofen or a derivative.

* * * * *